United States Patent [19]

Krämer et al.

[11] 3,940,414
[45] Feb. 24, 1976

[54] 1-PHENOXY-[IMIDAZOLYL-(1)]-2-HYDROXY-ALKANES

[75] Inventors: Wolfgang Krämer; Karl Heinz Büchel, both of Wuppertal; Paul-Ernst Frohberger; Hans Scheinpflug, both of Leverkusen, all of Germany

[73] Assignee: Bayer Aktiengesellschaft, Leverkusen, Germany

[22] Filed: June 17, 1974

[21] Appl. No.: 480,433

[30] Foreign Application Priority Data
June 30, 1973  Germany............................ 2333354

[52] U.S. Cl. .................. 260/309; 71/92; 424/273
[51] Int. Cl.² ...................................... C07D 233/60
[58] Field of Search ................................... 260/309

[56] References Cited
UNITED STATES PATENTS

| | | | |
|---|---|---|---|
| 3,531,494 | 9/1970 | Adolphi et al. | 260/309 |
| 3,575,999 | 4/1971 | Godefroi et al. | 260/309 |
| 3,641,047 | 2/1972 | Beaman et al. | 260/309 |
| 3,658,813 | 4/1972 | Godefroi et al. | 260/309 |
| 3,682,951 | 8/1972 | Kreider | 260/309 |
| 3,717,655 | 2/1973 | Godefroi et al. | 260/309 |

OTHER PUBLICATIONS
Metzger et al., Chem. Abst., 1972, Vol. 76, No. 140818s.

Sunjic et al., Chem. Abst., 1969, Vol. 70, No. 3945t.

*Primary Examiner*—Natalie Trousof
*Attorney, Agent, or Firm*—Burgess, Dinklage & Sprung

[57] ABSTRACT

Imidazolyls of the formula

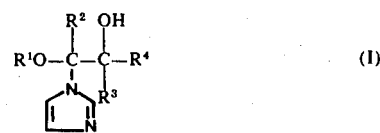

in which
R¹ is optionally substituted aryl,
R² is hydrogen, alkyl or optionally substituted aryl,
R³ is hydrogen, alkyl, alkenyl, cycloalkyl, optionally substituted aryl or optionally substituted aralkyl, and
R⁴ is alkyl, alkenyl, cycloalkyl, optionally substituted aryl or optionally substituted aralkyl, and their salts, which possess fungicidal and plant growth regulating properties.

6 Claims, No Drawings

1-PHENOXY-[IMIDAZOLYL-(1)]-2-HYDROXY-ALKANES

The present invention relates to and has for its objects the provision of particular new imidazolyl-O,N-acetals, i.e. 1-phenoxy-1-[imidazolyl-(1)]-2-hydroxyalkanes, which possess fungicidal and plant growth regulating properties, active compositions in the form of mixtures of such compounds with solid and liquid dispersible carrier vehicles, and methods for producing such compounds and for using such compounds in a new way especially for combating pests, e.g. fungi, and for regulating the growth of plants, with other and further objects becoming apparent from a study of the within specification and accompanying examples.

It has been disclosed in U.S. Pat. 3,321,366 that trityl-imidazoles such as triphenylimidazole (Compound A) possess fungicidal activity. However, their action is not always completely satisfactory, especially if low amounts and concentrations are used.

The present invention provides, as new compounds, the imidazolyl-O,N-acetals of the general formula

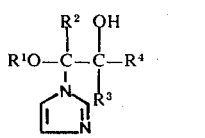

(I)

in which
R$^1$ is optionally substituted aryl,
R$^2$ is hydrogen, alkyl or optionally substituted aryl,
R$^3$ is hydrogen, alkyl, alkenyl, cycloalkyl, optionally substituted aryl or optionally substituted aralkyl, and
R$^4$ is alkyl, alkenyl, cycloalkyl, optionally substituted aryl or optionally substituted aralkyl,
and their salts.

Surprisingly, the active compounds according to the invention display a substantially higher fungicidal action than the known compound triphenylimidazole, which is chemically the nearest active compound. The active compounds according to the invention thus represent an enrichment of the art.

Preferably, R$^1$ is optionally monosubstituted or poly-(e.g., di-)substituted aryl with 6 to 10 carbon atoms, i.e. phenyl, especially with 6 carbon atoms, preferred substituents being halogen, especially fluorine, chlorine or bromine, straight-chain or branched alkyl with 1 to 6, especially 1 to 4, carbon atoms, alkoxy and alkylthio with, in either case, 1 to 4, especially 1 to 2, carbon atoms, halogenoalkyl with 1 to 2 carbon atoms and 1 to 5 halogen atoms, especially fluorine and chlorine, halogeno-alkoxy and halogenoalkylthio with, in either case, 1 or 2 carbon atoms and 3 to 5 halogen atoms, especially fluorine and chlorine (for example chlorodifluoromethylthio and chlorodifluoromethoxy), carbalkoxy with 1 to 4 carbon atoms in the alkoxy moiety o- and p-phenyl, and nitro; R$^2$ is hydrogen, straight-chain or branched alkyl with 1 to 6, especially 1 to 4, carbon atoms, or optionally monosubstituted phenyl with 6 to 10 carbon atoms, especially with 6 carbon atoms, preferred substituents being halogen, especially fluorine, chlorine or bromine, straight-chain or branched alkyl with 1 to 6, especially 1 to 4, carbon atoms, alkoxy and alkylthio with, in either case, 1 to 4, especially 1 or 2, carbon atoms, halogenoalkyl with 1 2 or 2 carbon atoms and 1 to 5 halogen atoms, especially fluorine and chlorine, halogenoalkoxy and halogenoalkylthio with, in either case, 1 or 2 carbon atoms and 3 to 5 halogen atoms, especially fluorine and chlorine (for example chlorodifluoromethylthio and chlorodifluoromethoxy), carbalkoxy with 1 to 4 carbon atoms in the alkoxy moiety, o- and p-phenyl, and nitro; R$^3$ is hydrogen, alkyl or alkenyl with up to 6, especially up to 4, carbon atoms, cycloalkyl with 5 to 6 carbon atoms, especially cyclohexyl, optionally substituted aryl with 6 to 10 carbon atoms, or optionally substituted aralkyl with 6 to 10 carbon atoms in the aryl moiety and 1 or 2 carbon atoms in the alkyl moiety, the preferred substituents being fluorine, chlorine, and alkyl and alkoxy, each with up to 4 carbon atoms; and R$^4$ is straight-chain or branched alkyl with 1 to 6, especially 1 to 4, carbon atoms, straight-chain or branched alkenyl with 2 to 6, especially 3 to 6, carbon atoms, cycloalkyl with 5 to 7, especially 5 to 6, carbon atoms, optionally monsubstituted or polysubstituted aryl with 6 to 10, especially 6, carbon atoms, or optionally monosubstituted or polysubstituted aralkyl with 6 to 10, especially 6, carbon atoms in the aryl moiety and 1 or 2 carbon atoms in the alkyl moiety, preferred substituents being halogen, especially fluorine, chlorine or bromine, straight-chain or branched alkyl with 1 to 6, especially 1 to 4, carbon atoms, alkoxy and alkylthio with, in either case, 1 to 4, especially 1 or 2, carbon atoms, halogenoalkyl with 1 or 2 carbon atoms and 1 to 5 halogen atoms, especially fluorine and chlorine, halogenoalkoxy and halogenoalkylthio with, in either case, 1 or 2 carbon atoms and 3 to 5 halogen atoms, especially fluorine and chlorine (for example chlorodifluoromethylthio and chlorodifluoromethoxy), carbalkoxy with 1 to 4 carbon atoms in the alkoxy moiety, o- and p-phenyl, and nitro.

The compounds of the formula (I) possess two asymmetrical carbon atoms and can therefore exist in the erythro form and in the threo form; in both cases, they are predominantly in the form of racemates.

The present invention also provides a process for the preparation of a compound of the formula (I), in which an imidazole derivative of the general formula

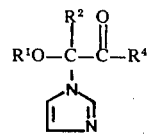

(II), in which
R$^1$, R$^2$ and R$^4$ have the above-mentioned meanings,
is (a) reduced with hydrogen in the presence of a catalyst and optionally in the presence of a polar solvent,
or (b) reduced with aluminum isopropylate in the presence of a solvent,
or (c) reduced with a complex hydride, optionally in the presence of a polar solvent,
or (d) reduced with formamidinesulfinic acid and alkali metal hydroxide, optionally in the presence of a polar solvent,
or (e) reacted in the presence of an inert solvent with an organo-metallic compound of the general formula

M-R$^3$ (III), in which
R$^3$ has the above-mentioned meaning and

M is an alkali metal (especially lithium or sodium) or an X-Mg radical ("Grignard group")
wherein
X is chlorine, bromine or iodine,
the imidazolyl-O,N-acetal produced in any of the process variants (a) to (e) being converted, if required, into a salt thereof.

If 1-phenoxy-1-[imidazolyl-(1)]-3,3-dimethylbutan-2-one and hydrogen are used as the starting materials in process variant (a), the course of the reaction can be represented by the following equation:

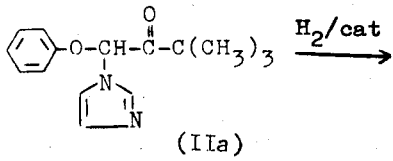

(IIa)

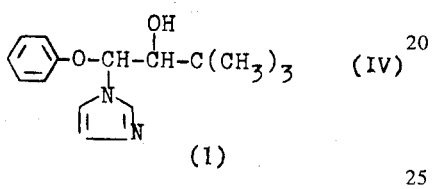

(1)

If 1-phenoxy-1-[imidazolyl-(1)]-3,3-dimethylbutan-2-one and aluminum isopropylate are used as the starting materials in process variant (b), the course of the reaction can be represented by the following equation:

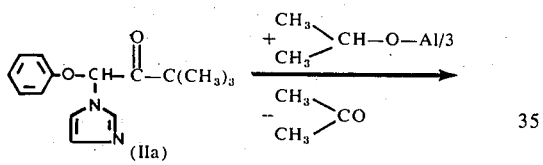

(IIa)

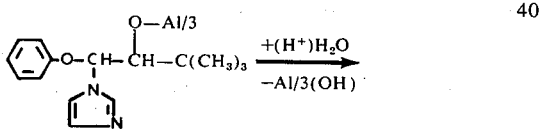

(1)

If 1-phenoxy-1-[imidazolyl-(1)]-3,3-dimethylbutan-2-one and sodium borohydride are used as the starting materials in process variant (c), the course of the reaction can be represented by the following equation:

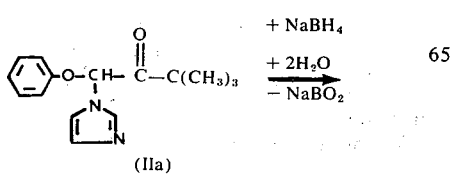

(IIa)

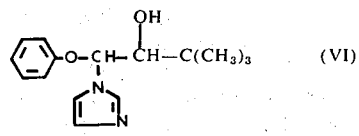

(1)

If 1-phenoxy-1-[imidazolyl-(1)]-3,3-dimethylbutan-2-one and formamidinesulfinic acid are used as the startingn materials in process variant (d), the course of the reaction can be represented by the following equation:

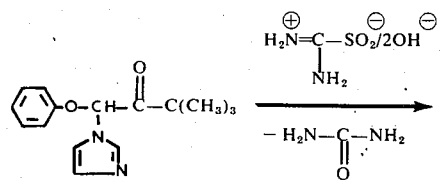

(IIa)

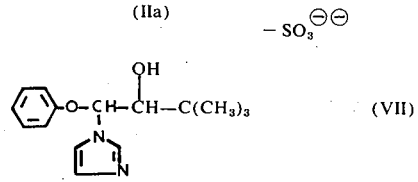

(1)

If 1-phenoxy-1-[imidazolyl-(1)]-3,3-dimethylbutan-2-one and methyl-magnesium iodide are used as the starting materials in process variant (e), the course of the reaction can be represented by the following equation:

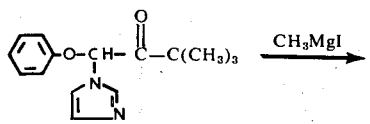

(IIa)

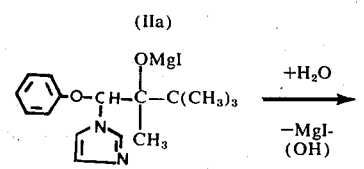

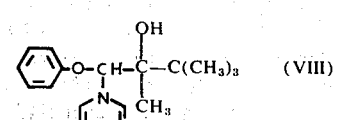

(17)

The following may be mentioned as examples of starting materials of the formula (II): 1-phenoxy-1-[imidazolyl-(1)]-3,3-dimethyl-butan-2-one, 1-(2'-chlorophenoxy)-1-[imidazolyl(1)]-3,3-dimethyl-butan-2-one, 1-(3'-chlorophenoxy)-1-[imidazolyl-(1)]-3,3-dimethyl-butan-2-one, 1-(4'-chlorophenoxy)-1-[imidazolyl-(1)]-3,3-dimethylbutan-2-one, 1-(4'-fluorophenoxy)-1-[imidazolyl-(1)]-3,3-dimethyl-butan-2-one, ω-(4'-chlorophenoxy)-ω-[imidazolyl-(1)]-acetophenone, ω-phenoxy-ω-[imidazolyl-(1)]-acetophenone, ω-phenoxy-ω-[imidazolyl-(1)]-propiophenone, 1-phenoxy-1-[imidazolyl(1)]-2-cyclohexyl-ethan-2-one, 1-(4'-bromophenoxy)-1-[imidazolyl-(1)]-3,3-dimethyl-butan-2-one, 1-(4'-methylphenoxy)-1-[imidazolyl(1)]-3,3-dimethyl-butan-2-one, 1-(4'-tert.butylphenoxy)-1-[imidazolyl-(1)]-3,3-dimethyl-butan-2-one, 1-(4'-diphenoxy)-1-[imidazolyl-(1)]-3,3-dimethyl-butan-2-one, 1-(2'-diphenoxy)-1-[imidazolyl-(1)]-3,3-dimethyl-butan-2-one, 1-(2',4'-dichlorophenoxy)-1-[imidazolyl-(1)]3,3-dimethyl-butan-2-one, 1-(2'-methyl-4'-chlorophenoxy)-1-[imidazolyl(1)]-3,3-dimethyl-butan-2-one, 1-(2',4',5'-trichlorophenoxy)-1-[imidazolyl-(1)]-3,3-dimethyl-butan-2-one, 1-(4'-nitrophenoxy)-1-[imidazolyl-(1)]-3,3-dimethyl-butan-2-one, 1-phenyl-1-(2',4'-dichlorophenoxy)-1-[imidazolyl-(1)]-3,3-dimethyl-butan-2-one and 1-methyl-1-(2',4'-dichlorophenoxy)-1-[imidazolyl-(1)]-3,3-dimethyl-butan-2-one.

The imidazole derivatives of the formula (II) which can be used according to the invention are disclosed in Patent application Ser. No. 219,556, filed Jan. 20, 1972, now U.S. Pat. 3,812,142.

Salts of compounds of the formula (I) which can be used are salts with physiologically tolerated acids. Preferred acids include the hydrogen halide acids, for example hydrobromic acid and, more especially, hydrochloric acid, phosphoric acid, monofunctional and bifunctional carboxylic acids and hydroxycarboxylic acids, for example acetic acid, maleic acid, succinic acid, fumaric acid, tartaric acid, citric acid, salicylic acid, sorbic acid and lactic acid, and 1,5-naphthalenedisulfonic acid.

Possible diluents for the reaction according to process variant (a) are polar organic solvents, especially alcohols, such as methanol and ethanol, and nitriles, such as acetonitrile. The reaction is carried out in the presence of a catalyst. Preferably, noble metal, noble metal oxide, noble metal hydroxide or Raney catalysts are used, especially platinum, platinum oxide and nickel. The reaction temperatures can be varied over a fairly wide range: in general, the reaction is carried out at between 20° and 50°C, preferably about 20° to 40°C. The reaction can be carried out not only under normal pressure, but also under elevated pressure, e.g. 1 or 2 atmospheres gauge. In the reaction according to process variant (a), about 1 mole of hydrogen and 0.1 mole of catalyst are generally employed per mole of the compound of the formula (II); to isolate the product, the catalyst is filtered off, the filtrate is freed from the solvent in vacuo and the resulting compounds of the formula (I) are purified by recrystallization. If desired, the salts of the compounds according to the invention are obtained according to customary methods.

If process variant (b) is used, preferred diluents for the reaction according to the invention are alcohols, such as isopropanol, or inert hydrocarbons, such as benzene. The reaction temperatures can again be varied over a fairly wide range; in general, the reaction is carried out at between 20° and 120°C, preferably at about 50° to 100°C. To carry out the reaction, about 1 to 2 moles of aluminum isopropylate are generally employed per mole of the compounds of the formula (II). To isolate the compounds of the formula (I), the excess salt is removed by distillation in vacuo and the resulting aluminum compound is decomposed with dilute sulfuric acid or sodium hydroxide solution. The further working up takes place in the customary manner.

If process variant (c) is used, possible diluents for the reaction are polar organic solvents, especially alcohols, such as methanol, ethanol, butanol and isopropanol, and ethers, such as diethyl ether or tetrahydrofuran. The reaction is generally carried out at 0° to 30°C, preferably about 0° to 20°C. For this reaction, about 1 mole of a complex hydride, such as sodium borohydride or lithium alanate, is generally employed per mole of the compounds of the formula (II). To isolate the compounds of the formula (I), the residue is taken up in dilute hydrochloric acid, subsequently rendered alkaline and extracted with an organic solvent. The further working up takes place in the customary manner.

Possible diluents for the reaction according to process variant (d) are polar organic solvents, especially alcohols, such as methanol and ethanol, as well as water. Here again, the reaction temperatures can be varied over a fairly wide range; the reaction is generally carried out at temperatures between 20° and 100°C, preferably about 50° to 100°C. To carry out the reaction, about 1 to 3 moles of formamidinesulfinic acid and 2 to 3 moles of alkali metal hydroxide are generally employed per mole of the compound of the formula (II). To isolate the end products, the reaction mixture is freed from the solvent and the residue is extracted with water and organic solvents, worked up in the usual manner, and purified; if desired, a salt is prepared.

In the reaction according to process variant (e), compounds of the general formula (I) in which $R^3$ is not hydrogen are obtained. In contrast thereto, the reactions according to process variants (a) to (d) are reduction reactions; the compounds of the formula (I) thereby obtained are secondary alcohols in which $R^3$ is hydrogen only.

The organo-metallic compounds of the formula (III) are in general known; a summary and review of numerous publications is to be found, for example, in G. E. Coates, "OrganMetallic Compounds", 2nd edition, Methuen and Co., London (1960).

For the reaction according to process variant (e), anhydrous ethers, such as diethyl ether and dibutyl ether are preferably used as reaction media. The reaction temperatures will generally be between 0° and 80°C, preferably about 30° to 60°C. In carrying out process variant (e), about 1 mole of the organo-metallic compound of the formula (III) is generally employed per mole of the compound of the formula (II). The mixtures obtained by organo-metallic reactions are worked up in the customary and generally knwon manner.

The active compounds according to the invention display a strong fungitoxic action. They do not harm crop plants in the concentrations required to combat fungi. For these reasons, they are suitable for use as plant protection agents for combating fungi. Fungitoxic agents in plant protection are employed for combating Archimycetes, Phycomycetes, Ascomycetes, Basidiomycetes and *Fungi Imperfecti*.

The active compounds according to the invention have a very broad spectrum of action and can be used against parasitic fungi which attack the above-ground parts of plants or attack the plants through the soil, and against seed-borne pathogens.

The active compounds according to the invention display a particularly good action against parasitic fungi on above-ground parts of plants, such as species of Erysiphe, species of Podosphaera, species of Venturia and also species of Piricularia and species of Pellicularia.

It should be emphasised that the active compounds according to the invention not only display a protective action but are also curatively active, that is to say they can also be employed after infection has taken place. In addition, the systemic action of the compounds should be pointed out. Thus it proves possible to protect plants against fungal attack by supplying the active compound to the above-ground parts of plants through the soil, through the plant or through the seed. As plant protection agents, the active compounds according to the invention can be used for the treatment of seed and for the treatment of above-ground parts of plants.

The active compounds according to the invention are well tolerated by plants. They have only a low toxicity towards warm-blooded animals and because of their low odor and good toleration by human skin they are not unpleasant to handle.

The active compounds according to the invention furthermore display a plant-growth-regulating activity.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and plant growth regulating agents, or insecticides, acaricides, bactericides, rodenticides, nematocides, herbicides, bird repellents, fertilizers, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 1–95% by weight, and preferably 5–90% by weight, of the mixture, whereas carrier composition mixtures suitable for direct application or field application generally contemplate those in which the active compound is present in an amount substantially between about 0.00001–10%, preferably 0.001–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used as leaf fungicides, the active-compound concentrations in the application forms can be varied within a fairly wide range. They are generally between 0.1 and 0.00001 per cent by weight and preferably between 0.05 and 0.0001 per cent.

For the treatment of seed, amounts of active compound of 0.001 to 50 g per kilogram of seed, preferably 0.01 to 10 g, are generally required.

Furthermore, the present invention contemplates methods of selectively killing, combating or controlling pests, e.g. fungi, and methods of regulating the growth of plants, which comprises applying to at least one of correspondingly (a) such fungi, (b) such plants and (c) the corresponding habitat thereof, i.e. the locus to be treated, a correspondingly combative or toxic amount, i.e. a fungicidally or plant growth regulating effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend on the intended application. Therefore, in special cases it is possible to go above or below the aforementioned concentration ranges.

The synthesis, unexpected superiority and outstanding activity of the particular new compounds of the present invention are illustrated, without limitation, by the following examples.

EXAMPLE 1

Erysiphe test/systemic
Solvent: 4.7 parts by weight of acetone
Dispersing agent: 0.3 part by weight of alkylaryl polyglycol ether
Water: 95 parts by weight The amount of active compound required to give the desired concentration of active compound in the watering liquid was mixed with the stated amount of solvent and the concentrate was diluted with the stated amount of water which contained the stated additives.

Cucumber plants grown in standard soil, in the 1–2 leaf stage, were watered three times within one week with 20 ml of the watering liquid, of the stated concentration of active compound, per 100 ml of soil.

The plants treated in this way were inoculated, after treatment, with conidia of the fungus *Erysiphe cichoracearum*. The plants were then set up in a greenhouse at 23°–24°C and 70% relative atmospheric humidity. After 12 days, the infection of the cucumber plants was determined as a percentage of the untreated, but also inoculated, control plants.

0% denotes no infection and 100% denotes that the infection was exactly as great as in the case of the control plants.

The active compounds, active-compound concentrations and results can be seen from the table which follows:

Table 1

| Active compound | Erysiphe test / systemic — Infection in % of the infection of the untreated control at an active compound concentration of 100 ppm |
|---|---|
| (A) (known) — triphenyl-imidazole structure | 75 |
| Br–⟨C₆H₄⟩–O–CH(N-imidazolyl)–CH(OH)–C(CH₃)₃ (4) | 54 |
| Cl–⟨C₆H₄⟩–O–CH(N-imidazolyl)–CH(OH)–C(CH₃)₃ (3) | 25 |
| 2,4-Cl₂–⟨C₆H₃⟩–O–CH(N-imidazolyl)–CH(OH)–C(CH₃)₃ (11) | 54 |

EXAMPLE 2

Shoot treatment test/powdery mildew of cereal/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier, and then 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of *Erysiphe graminis* var. *hordei*.

After 6 days' dwell time of the plants at a temperature of 21°–22°C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The active compound is the more active, the lower the degree of rust infection.

The active compounds, active-compound concentration in the spray liquor and degrees of infection can be seen from the table which follows:

and then 975 parts by weight of water were added. The concentrate was diluted with water to the desired final concentrations of the spray liquor.

To test for curative activity, the procedure followed was analogous to that in Example 2, but in converse sequence. The treatment of the single-leaved young Table 2

Shoot treatment test/powdery mildew of cereal/protective

| Active compounds | Active compound concentration in the spray liquor in % by weight | Infection in % of the untreated control |
|---|---|---|
| untreated | — | 100.0 |
| 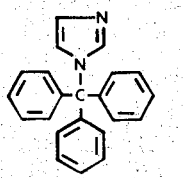 (known) | 0.001 | 100.0 |
| 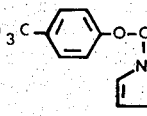 (6) | 0.001 | 33.8 |
| 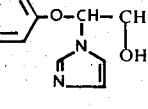 (4) | 0.001<br>0.0005 | 0.0<br>41.3 |
| 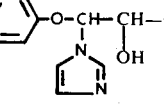 (3) | 0.001<br>0.0005 | 10.0<br>41.3 |
| 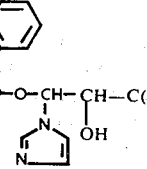 (7) | 0.001 | 25.0 |

EXAMPLE 3

Shoot treatment test/powdery mildew of cereal/curative (leaf-destructive mycosis)

To produce a suitable preparation of active compound, 0.25 part by weight of active compound was taken up in 25 parts by weight of dimethylformamide and 0.06 part by weight of alkylaryl polyglycol ether barley plants with the preparation of active compound took place 48 hours after the inoculation, when the infection was already manifest.

After 6 days' dwell time of the plants at a temperature of 21°–22°C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The active compound is the more active, the lower the degree of infection with rust.

The active compounds, active-compound concentrations in the spray liquor and degrees of infection can be seen from the table which follows.

Table 3

Shoot treatment test/cereal mildew/curative

| Active compounds | | Active compound concentration in the spray liquor in % by weight | Infection in % of the untreated control |
|---|---|---|---|
| untreated | | — | 100.0 |
| Br—⟨⟩—O—CH—CH—C(CH₃)₃ <br>                N   OH | (4) | 0.01 <br> 0.001 | 0.0 <br> 0.0 |
| Cl—⟨⟩—O—CH—CH—C(CH₃)₃ <br>                N   OH | (3) | 0.01 <br> 0.001 | 0.0 <br> 6.3 |
| (triphenyl-imidazolyl-methane structure) (known) | | 0.01 | 87.5 |

The process of the present invention is illustrated in the following preparative Examples.

EXAMPLE 4

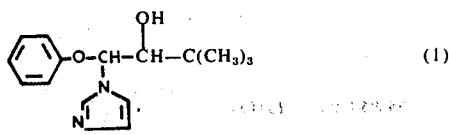

(1)

Method (a)

25.8 (0.1 mole) of 1-phenoxy-1-[imidazolyl-(1)]-3,3-dimethyl-butan-2-one were dissolved in 250 ml of methanol and 5.9 g (0.15 mole) of sodium borohydride were introduced in portions into this solution at 5° to 10°C while stirring and using a reflux condenser. After stirring for 15 hours at room temperature, 20 ml of concentrated hydrochloric acid were added and the reaction mixture was stirred for a further 15 hours at room temperature and then poured into 300 ml of saturated sodium bicarbonate solution. The mixure was extracted twice with 100 ml of methylene chloride, the combined organic phases were washed twice with 100 ml of water and dried over sodium sulfate, and the solvent was distilled off in a water pump vacuum. The residue was triturated with 30 ml of petroleum ether.

21.6 g (83% of theory) of 1-phenoxy-1-[imidazolyl-(1)]-2-hydroxy-3,3-dimethyl-butane of melting point 99°–105°C (a mixture of the erythro form and threo form) were obtained.

Method (b)

12.3 g (0.048 mole) of 1-phenoxy-1-[imidazolyl-(1)]-3,3-dimethyl-butan-2-one were dissolved in 50 ml of anhydrous ether. This solution was added dropwise to a suspension of 2.6 g (0.07 mole) of lithium aluminum hydride in 80 ml of anhydrous ether and the reaction mixture was heated for one hour under reflux and left to stand overnight. Water was then added dropwise to the reaction mixture, while cooling with ice, in order to destroy excess lithium aluminum hydride. The mixture was then introduced into 20% strength cold sodium hydroxide solution and extracted twice with 100 ml of ether. The combined organic phases were dried over sodium sulfate and the solvent is distilled off in vacuo. The resulting oil was boiled up with petroleum ether, whereupon it crystallized. The precipitate was filtered off hot.

1.6 g (13% of theory) of erythro-1-phenoxy-1-[imidazolyl-(1)]-2-hydroxy-3,3-dimethyl-butane of melting point 125°C were obtained.

The filtrate was cooled. This again produced a precipitate, which was filtered off. From this fraction, 1.4 g (11% of theory) of threo-1-phenoxy-[1-imidazolyl- (1)]-2-hydroxy-3,3-dimethyl-butane of melting point 106°–107°C were obtained.
The compounds listed in Table 4 which follows were prepared analogously:
Table 4
| Compound No. | R¹ | R² | R³ | R⁴ | Melting point, °C | Method |
|---|---|---|---|---|---|---|
| 2 |  | H | H | $C(CH_3)_3$ | 116 | (a) |
| 3 |  | H | H | $C(CH_3)_3$ | 145–147 | (a) |
| 4 |  | H | H | $C(CH_3)_3$ | 173–174 | (a) |
| 5 | 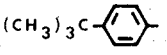 | H | H | $C(CH_3)_3$ | 103–105 | (a) |
| 6 |  | H | H | $C(CH_3)_3$ | 145–150 | (a) |
| 7 |  | H | H | $C(CH_3)_3$ | 127–129 | (a) |
| 8 |  | H | H | $C(CH_3)_3$ | 136–148 | (a) |
| 9 |  | H | H | $C(CH_3)_3$ | 101–109 | (a) |
| 10 |  | H | H | $C(CH_3)_3$ | hydrochloride 190–210 | (a) |
| 11 |  | H | H | $C(CH_3)_3$ | 95–102 | (a) |
| 12 |  |  | | $C(CH_3)_3$ | 159–160 | (b) |
| 13 | Cl—⟨⟩— | H | $CH_3$ | $C(CH_3)_3$ | 162–163 | (c)* |
| 14 | 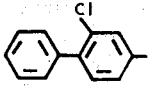 | H | H | $C(CH_3)_3$ | 89–95 | (a) |

Table 4-continued $$R^1O-\underset{\underset{\underset{N}{\big|}}{\overset{R^2}{\big|}}}{C}-\underset{\underset{R^3}{\big|}}{\overset{OH}{\overset{\big|}{C}}}-R^4 \quad (I)$$
(with imidazolyl ring on N)

| Compound No. | R¹ | R² | R³ | R⁴ | Melting point, °C | Method |
|---|---|---|---|---|---|---|
| 15 | 3,4-dichlorophenyl | H | H | C(CH₃)₃ | 110–113 | (a) |
| 16 | 4-iodophenyl | H | H | C(CH₃)₃ | 102–4 | (a) |

*Compound (13) was prepared in accordance with Method as follows;

To a suspension of 4.8 g (0.22 mole) magnesium turnings in 50 ml of anhydrous ether were added dropwise 31.2 g (0.22 mole) methyl iodide in 100 ml of anhydrous ether while stirring and using a reflux condenser. After the addition, a solution of 29.3 g (0.1 mole) 1-(4'-chlorophenoxy)-1-[imidazolyl-(1)]-3,3-dimethyl-butan-2-one in 100 ml of anhydrous ether was added dropwise. The mixture was refluxed for 18 hours. After cooling the mixture was introduced into a solution of 80 g ammonium chloride in 600 ml of water. After addition of ethyl acetate and subsequent stirring, the organic layer was separated, washed with water and dried. After evaporation of the solvent, the residue was digested in hot petroleum ether, remaining undissolved, and filtered off hot. 11 g (36% of theory) of 1-(4'-chlorophenoxy)-1-[imidazolyl-(1)]-2-hydroxy-3,3-dimethyl-butane of melting point 162°–163°C were obtained.

In an analogous manner the following compounds can be prepared:

| R¹ | R² | R³ | R⁴ | Method |
|---|---|---|---|---|
| 2-methoxyphenyl | H | H | C(CH₃)₃ | (a) |
| 2-fluorophenyl | H | H | C(CH₃)₃ | (b) |
| 2-bromophenyl | H | H | C(CH₃)₃ | (b) |
| 4-(CH₃O–CO)phenyl | H | H | C(CH₃)₃ | (a) |
| 4-(CH₃–S)phenyl | H | H | C(CH₃)₃ | (a) |
| 3-trifluoromethylphenyl | H | H | C(CH₃)₃ | (a) |
| 4-(CF₃O)phenyl | H | H | C(CH₃)₃ | (a) |

-continued

| R¹ | R² | R³ | R⁴ | Method |
|---|---|---|---|---|
| ClCF₂S—C₆H₄— | H | H | C(CH₃)₃ | (a) |
| O₂N—C₆H₄— | H | CH₃ | C(CH₃)₃ | (c) |
| Cl—C₆H₄— | CH₃—C₆H₄— | H | C(CH₃)₃ | (a) |
| Cl—C₆H₄— | H | H | cyclohexyl | (a) |
| 2,Cl-Cl—C₆H₃— | H | H | cyclohexyl | (a) |
| Cl—C₆H₄— | H | H | CH₃ | (a) |
| Cl—C₆H₄— | C(CH₃)₃ | H | CH₃ | (a) |
| Cl—C₆H₄— | H | H | C₆H₅ | (a) |
| C₆H₅— | H | H | C₆H₄—Cl | (a) |
| Cl—C₆H₄— | H | C₆H₅—CH₂— | C(CH₃)₃ | (c) |
| C₆H₅— | H | —CH₂—CH=CH₂ | C(CH₃)₃ | (c) |

It will be appreciated that the instant specification and examples are set forth by way of illustration and not limitation, and that various modifications and changes may be made without departing from the spirit and scope of the present invention.

What we claim is:
1. An imidazole of the formula

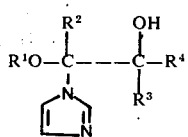

in which
R¹ is optionally monosubstituted or disubstituted phenyl the substituents being selected from halogen, straight-chain or branched alkyl with 1 to 6 carbon atoms, alkoxy and alkylthio with, in either case, 1 to 4 carbon atoms, halogenoalkyl with 1 or 2 carbon atoms and 1 to 5 halogen atoms, halogenoalkoxy and halogenoalkylthio with, in either case, 1 or 2 carbon atoms and 3 to 5 halogen atoms, carbalkoxy with 1 to 4 carbon atoms in the alkoxy moiety, o- and p-phenyl, and nitro;

R² is hydrogen, straight-chain or branched alkyl with 1 to 6 carbon atoms or optionally monosubstituted phenyl, the substituents being selected from halogen, straight-chain or branched alkyl with 1 to 6 carbon atoms, alkoxy and alkylthio with, in either case, 1 to 4 carbon atoms, halogenoalkyl with 1 or 2 carbon atoms and 1 to 5 halogen atoms, halogenoalkoxy and halogenoalkylthio with, in either case, 1 or 2 carbon atoms and 3 to 5 halogen atoms, carbalkoxy with 1 to 4 carbon atoms in the alkoxy moiety, o- and p-phenyl, and nitro;

$R^3$ is hydrogen, alkyl or alkenyl with up to 6 carbon atoms, cycloalkyl with 5 to 6 carbon atoms, optionally substituted benzyl, the substituents being selected from fluorine, chlorine and alkyl and alkoxy, each with up to 4 carbon atoms; and $R^4$ is straight-chain or branched alkyl with 1 to 6 carbon atoms, straight-chain or branched alkenyl with 2 to 6 carbon atoms, cycloalkyl with 5 to 7 carbon atoms, optionally substituted phenyl, the substituents being selected from fluorine, chlorine and alkyl and alkoxy each with up to 4 carbon atoms, or a salt thereof with fungicidal or plant growth-regulating activity.

2. The compound according to claim 1 wherein such compound is 1-p-chlorophenoxy-1-[imidazolyl-(1)]-2-hydroxy-3,3-dimethy-butane of the formula

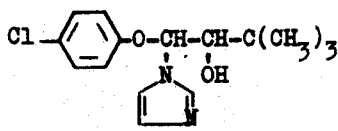

or a salt thereof.

3. The compound according to claim 1 wherein such compound is 1-p-bromophenoxy-1-[imidazolyl-(1)]-2-hydroxy-3,3-dimethyl-butane of the formula

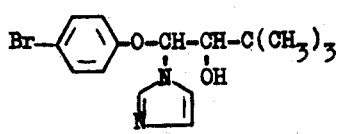

or a salt thereof.

4. The compound according to claim 1 wherein such compound is 1-p-fluorophenoxy-1-[imidazolyl-(1)]-2-hydroxy-3,3-dimethyl-butane of the formula

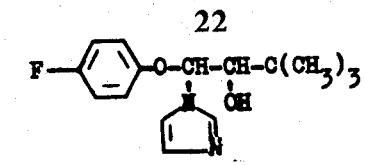

or a salt thereof.

5. The compound according to claim 1 wherein such compound is 1-o,p-dichlorophenoxy-1-[imidazolyl-(1)]-2-hydroxy-3,3-dimethyl-butane of the formula

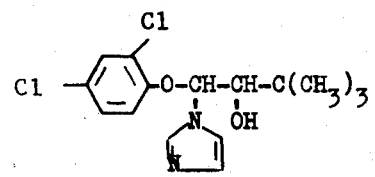

or a salt thereof.

6. The compound according to claim 1 wherein such compound is 1-o,p-dichlorophenoxy-1-[imidazolyl-(1)]-1-phenyl-2-hydroxy-3,3-dimethyl-butane of the formula

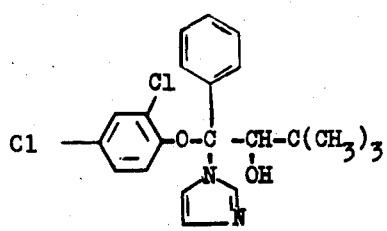

or a salt thereof.

* * * * *